United States Patent [19]
Rauchschwalbe et al.

[11] Patent Number: 4,990,686
[45] Date of Patent: Feb. 5, 1991

[54] PROCESS FOR THE PURIFICATION OF CRUDE 2,2-BIS-(3,5-DIMETHYL-4-HYDROXY-PHENYL)-PROPANE

[75] Inventors: Günter Rauchschwalbe, Leverkusen; Heinz-Ulrich Blank, Odenthal; Volkmar Handschuh, Burscheid, all of Fed. Rep. of Germany

[73] Assignee: Bayer Aktiengesellschaft, Leverkusen, Fed. Rep. of Germany

[21] Appl. No.: 457,419

[22] Filed: Dec. 27, 1989

[30] Foreign Application Priority Data

Jan. 12, 1989 [DE] Fed. Rep. of Germany ....... 3900680

[51] Int. Cl.$^5$ ............................................. C07C 37/84
[52] U.S. Cl. ..................................... 568/724; 568/722; 568/727
[58] Field of Search ................ 568/722, 723, 724, 727

[56] References Cited

U.S. PATENT DOCUMENTS

| 4,242,527 | 12/1980 | Mark et al. | 568/724 |
| 4,320,234 | 3/1982 | Mark et al. | 568/724 |
| 4,414,422 | 11/1983 | Ash et al. | 568/724 |

FOREIGN PATENT DOCUMENTS

| 2758565 | 7/1978 | Fed. Rep. of Germany | 568/724 |
| 2758566 | 7/1978 | Fed. Rep. of Germany | 568/724 |
| 2749278 | 5/1979 | Fed. Rep. of Germany | 568/724 |
| 2853883 | 7/1979 | Fed. Rep. of Germany | 568/724 |
| 1323066 | 7/1973 | United Kingdom | 568/724 |

Primary Examiner—Werren B. Lone
Attorney, Agent, or Firm—Sprung Horn Kramer & Woods

[57] ABSTRACT

Crude 2,2-bis-(3,5-dimethyl-4-hydroxyphenyl)propane (=tetramethyl-bisphenol A=TMBPA) can be purified by recrystallization, if $C_1$–$C_4$-monoalcohols with a water content of 2 to 40% by weight relative to the total weight of alcohol and water are used in an amount of 70 to 250% by weight, relative to the amount of TMBPA and the recrystallization is carried out at a temperature of 65° to 150° C.

15 Claims, No Drawings

PROCESS FOR THE PURIFICATION OF CRUDE 2,2-BIS-(3,5-DIMETHYL-4-HYDROXYPHENYL)-PROPANE

BACKGROUND OF THE INVENTION

The present invention relates to a process for the purification of crude 2,2-bis-(3,5-dimethyl-4-hydroxyphenyl)-propane (= tetramethyl-bisphenol A = TMBPA) by recrystallization from aqueous solutions of alcohols.

In principle, it is known to recrystallize bisphenols from aqueous solutions of lower alcohols. DE-OS (German Published Specification) 2,758,565 describes for this purpose chiefly glycols or ethers thereof, and glycerol, phenol and ethanolamine as alcoholic solvents. which are to be used. These solvents however are recoverable only with difficulty and are not allowed to enter waste water due to their toxicity (for example toxicity to fish) but must be disposed of separately. The said DE-OS also specifies a solvent mixture comprising ethanol and water in the example of bisphenol A which is to be recrystallized. In this recrystallization, an amount of 500 g of water and 102 g of ethanol are used per 50 g of bisphenol A, in order to completely dissolve the bisphenol A at 100° C. Thus more than 600 g of solvent in total are necessary per 50 g of the bisphenol A which is to be recrystallized. Obviously, the purification process of the above DE-OS is based on the notion that mainly a poor solvent with a high water content must be used in order to minimize crystallization losses.

However, TMBPA cannot be recrystallized under these conditions.

SUMMARY OF THE INVENTION

It has now been found that in the case of TMBPA, in contrast to the described teaching, the ratio of alcohol to water can be greatly increased and at the same time the ratio of the aqueous solution of alcohol to TMBPA can be considerably reduced, this enabling the space yield of this process to be considerably increased and high recoveries of recrystallized pure TMBPA nevertheless to be achieved. This was not to be expected from the greater solvent power of an alcohol/water mixture of this type. A lower recovery would inevitably be accompanied by increased contamination of the waste water being produced. Both effects would stand in the way of an economical process.

Accordingly, it was surprisingly found that for example a mixture of 30 g of water and 120 g of methanol at 100° C. dissolves at least 95 g of pure TMBPA and, when the solution is cooled, 92% of the TMBPA used is recovered. Relative to the amount of substrate used, this is less than a quarter of the total amount of solvent mixture which is required according to the aforesaid DE-OS, and at the same time is only about 60% of the amount of alcoholic solvent from this DE-OS. At the same time, the recovered substrate is very much more pure than that described in the aforesaid DE-OS. Thus according to this DE-OS an enrichment from 93.1% to 96.0% in desired p,p'-isomers is achieved while in the present process an enrichment from 93-95% to 99.7% is achieved, for example. Such results were not expected with regard to the known prior art.

The invention therefore relates to a process for the purification of crude 2,2-bis-(3,5-dimethyl-4-hydroxyphenyl)-propane (=tetramethyl-bisphenol A= TMBPA) by recrystallization from aqueous solutions of alcohols, characterized in that a $C_1$–$C_4$-monoalcohol with a water content of 2 to 40% by weight relative to the total weight of alcohol and water is used in an amount of from 50 to 250% by weight relative to the amount of TMBPA, and the operation is carried out at a temperature of 65° C. to 150° C.

DETAILED DESCRIPTION OF THE INVENTION

Alcohols for the process according to the invention are methanol, ethanol, propanol, isopropanol, butanol, isobutanol or tert.-butanol, preferably a $C_1$–$C_3$-monoalcohol, such as methanol, ethanol, propanol or isopropanol, particularly preferably methanol or ethanol and most particularly preferably methanol.

The total amount of solvent contains 2 to 40% by weight of water, preferably 5 to 40% by weight, particularly preferably 10 to 30% by weight and most particularly preferably 15 to 25% by weight of water. This solvent mixture is used in an amount of from 50 to 250% by weight, relative to the amount of TMBPA which is to be recrystallized, preferably in an amount of from 50 to 200% by weight, particularly preferably in an amount of from 80 to 150% by weight.

The recrystallization according to the invention is carried out at a temperature of 65° C. to 150° C., preferably at 80° C. to 120° C. If the boiling point of the monoalcohol used is exceeded, the operation is carried out under elevated pressure. Such pressures are accordingly from 1 to 20 bar, preferably 1.2 to 5 bar. This pressure can be the autogenous pressure of the total recrystallization system or pressure from another source, for example due to compressed nitrogen. Preferably the operation is carried out under the prevailing autogenous pressure. In many cases it can be advantageous to fill the pressure vessel which is needed for this purpose with the whole batch of TMBPA which is to be recrystallized and with the solvent mixture, to heat the mixture until (close to) the boiling point and only then to pressure-seal the vessel. In this way, the total pressure is reduced by the absence of the partial pressure of air.

A further advantageous procedure comprises taking initially the alcohol component of the solvent mixture and suspending the TMBPA therein. The suspension is then heated to the boiling point and only then is the water component added, and, depending on the mixture ratios which have been selected, pure TMBPA can already separate out at this point; in each case however the whole recrystallization system is cooled to room temperature with stirring. Depending on the quality of the crude TMBPA it can also be advantageous to treat the hot solution of TMBPA with clarifying agents, such as inter alia active charcoal, kieselguhr, silica gel, or cellulose powder, to filter off these clarifying agents and only then to cool the solution with stirring. When carrying out this operation the addition of water can take place before or after a filtration of this type.

It can also be advantageous to add soluble substances which act as reducing agents. Such substances are for example sulphites, hydrogen sulphites, dithionites or boranates of alkali metals or alkaline earth metals, preferably of sodium. Rongalite may be mentioned as another reducing agent. Reducing agents of this type are added in an amount of from 0.1 to 5% by weight, preferably 0.5 to 2% by weight, relative to TMBPA. Preferably sodium dithionite or rongalite are added.

The TMBPA obtained in the process according to the invention is pure white, readily filterable and of high purity. TMBPA is a starting material for the preparation of engineering thermoplastics.

EXAMPLE 1

A mixture of 600 ml (480 g) of methanol, 120 ml of water, 1 g of $Na_2S_2O_4$ and 400 g of technical grade (about 95% pure) red-coloured TMBPA was heated to about 100° C. in an autoclave with stirring. During this operation, a pressure of about 2 bar was reached. The mixture was cooled with stirring and filtered. The filter cake was initially washed with 50% strength methanol, then with water and dried. 350 g of pure white TMBPA were obtained, with a content of 99.7% by weight according to gas chromatographic analysis and a m.p. of 166.5 to 167.5° C. This represented a recovery of 92% of the TMBPA present in the original material. The mother liquor was worked up by distillation in order to recover the solvent. The residue (suspension in water) was filtered off. The solid residue was disposed of by burning; the aqueous waste was readily biodegradable.

EXAMPLE 2

A mixture of 250 g of 95% strength TMBPA. and 250 g of 70% strength methanol (175 g of MeOH +75 g of $H_2O$) and 1.2 g of $Na_2S_2O_4$ was heated to about 100° C. in a glass autoclave. During this operation the TMBPA was completely dissolved. A pressure of about 1.9 bar was reached. The solution was cooled to room temperature. After working up (as in Example 1) 227 g of white TMBPA (99.6% pure) were obtained; this corresponds to a recovery of 95%; the yield achieved is about 420 g/l.

EXAMPLE 3

A mixture of 250 g of 95% strength TMBPA and 250 g of 90% ethanol (225 g of EtOH +25 g of $H_2O$) and 1.2 g of $Na_2S_2O_4$ was heated to 97° C. in a glass autoclave. During this operation the TMBPA was completely dissolved. A pressure of 1.4 bar was reached. The solution was cooled to room temperature. After working up (as in Example 1) 191 g of white TMBPA (99.8% pure) were obtained; this corresponds to a recovery of 80%.

EXAMPLE 4

A mixture of 300 g of 95% strength TMBPA (=285 g/100%), 285 g of 70% strength 2-propanol (200 g of 2-propanol +85 g of $H_2O$) and 1.2 g of $Na_2S_2O_4$ was heated to 102° C. in a glass autoclave. During this operation the TMBPA was completely dissolved; a pressure of 1.3 bar was reached. The solution was cooled and (after working up as in Example 1) 263 g of 99.5% strength TMBPA were isolated. This corresponds to a recovery of 92%.

EXAMPLE 5

200 g of methanol were heated to boil under reflux in an open vessel, 140 g of pure TMBPA were dissolved therein, the latter being completely dissolved directly, and 40 g of water were added dropwise to the boiling solution. The mixture was cooled to 25° C. and 125 g of TMBPA were isolated (recovery 89%).

What is claimed is:

1. A process for the purification of crude 2,2-bis-(3,5-dimethyl-4-hydroxyphenyl)-propane (= tetramethyl-bisphenol A=TMBPA) by recrystallization from aqueous solutions of alcohols, wherein a $C_1$-$C_4$-monalcohol with a water content of 2 to 40% by weight relative to the total weight of alcohol and water is used in an amount of from 50 to 250% by weight relative to the amount of TMBPA, and the operation is carried out at a temperature of 65 to 150° C.

2. The process of claim 1, wherein a $C_1$-$C_3$-monalcohol is used.

3. The process of claim 2, wherein methanol or ethanol is used.

4. The process of claim 3, wherein methanol is used.

5. The process of claim 1, wherein the total amount of solvent contains 5 to 40% by weight of water.

6. The process of claim 5, wherein the total amount of solvent contains 10 to 30% by weight of water.

7. The process of claim 6, wherein the total amount of solvent contains 15 to 25% by weight of water.

8. The process of claim 1, wherein the solvent mixture is used in an amount of from 50 to 200% by weight, relative to the TMBPA which is to be recrystallized.

9. The process of claim 8, wherein the solvent mixture is used in an amount of from 80 to 150% by weight, relative to the TMBPA which is to be recrystallized.

10. The process of claim 1, operated at a temperature of 80 to 120° C.

11. The process of claim 10, operated at a pressure of 1 to 10 bar.

12. The process of claim 11, operated at a pressure of 1.2 to 5 bar.

13. The process of claim 12, operated at the autogenous pressure of the system.

14. The process of claim 1, operated in the presence of soluble, reducing agent additives in an amount of from 0.1 to 5% by weight, relative to TMBPA.

15. The process of claim 14, operated in the presence of sodium dithionite or rongalite.

* * * * *